United States Patent [19]

Menezes et al.

[11] Patent Number: 4,620,542

[45] Date of Patent: * Nov. 4, 1986

[54] ETHYLENE-PROPYLENE COPOLYMER SUTURES

[75] Inventors: Edgar Menezes, Somerville; Peter Steinheuser, Manville, both of N.J.

[73] Assignee: Ethicon, Inc., Somerville, N.J.

[ * ] Notice: The portion of the term of this patent subsequent to Jun. 4, 2002 has been disclaimed.

[21] Appl. No.: 652,705

[22] Filed: Sep. 21, 1984

Related U.S. Application Data

[63] Continuation-in-part of Ser. No. 432,487, Oct. 4, 1982, abandoned, and Ser. No. 531,246, Sep. 13, 1983, Pat. No. 4,520,822.

[51] Int. Cl.$^4$ ............................................. A61L 17/00
[52] U.S. Cl. ............................... 128/335.5; 428/364; 523/114
[58] Field of Search ............................ 128/334, 335.5; 523/114; 428/364, 370, 394, 395, 396, 397, 398

[56] References Cited

U.S. PATENT DOCUMENTS 4,520,822  6/1985  Menezes et al. ..................... 428/364

Primary Examiner—John Kight
Assistant Examiner—Kriellion Morgan
Attorney, Agent, or Firm—Charles J. Metz

[57] ABSTRACT

Sterile surgical monofilament sutures are disclosed. The sutures are made from ethylene-propylene copolymers, and have improved compliance, compared with polypropylene homopolymer sutures.

6 Claims, No Drawings

ETHYLENE-PROPYLENE COPOLYMER SUTURES

This application is a continuation-in-part of our applications Ser. No. 432,487, filed Oct. 4, 1982, now abandoned, and Ser. No. 531,246, filed Sept. 13, 1983, now U.S. Pat. No. 4,520,822.

The invention relates to surgical sutures made from ethylene-propylene copolymers.

BACKGROUND OF THE INVENTION

Surgical sutures made from polypropylene have been successfully used by the medical profession for more than ten years. The advantages exhibited by polypropylene sutures include the following:

(a) They pass easily through tissue;
(b) They resist breakdown and do not promote infection;
(c) They provide good knot security;
(d) They have minimal reaction with tissue;
(e) They have high tensile strength; and
(f) They maintain their in vivo tensile strength over extended periods.

The preferred polypropylene suture used in the medical profession today is described by Listner in U.S. Pat. No. 3,630,205. The polypropylene sutures described by Listner have the following properties:

| | |
|---|---|
| Tensile Strength (45,000 to 100,000 psi) | 3.9 to 8.9 grams/denier |
| Knot Strength (38,000 to 91,000 psi) | 3.3 to 7.9 grams/denier |
| Break Elongation | 36 to 62% |
| Young's Modulus | 313,000 to 523,000 psi |

As good as the current polypropylene sutures are, there is some room for improvement. In particular, it would be desirable to increase the compliance, limpness, or flexibility of polypropylene sutures in order to make them easier to tie and to improve their knot security. The problem is that previous efforts to accomplish this have occasioned a concomitant undesirable decrease in strength properties.

The present invention is based upon the discovery that surgical sutures can be made from certain ethylene-propylene copolymers, and that such sutures retain to a large degree the excellent properties of polypropylene sutures, but, at the same time, are more compliant and are therefore easier for the surgeon to tie.

BRIEF OUTLINE OF THE INVENTION

The invention provides surgical sutures made from ethylene-propylene copolymers, such copolymers containing a small amount, for instance, from about 0.3 to about 7, and preferably from about 0.5 to about 5, weight percent, copolymerized ethylene, when the copolymer is a random copolymer, and from about 2 to about 15, and preferably from about 4 to about 10, weight percent, copolymerized ethylene, when the copolymer is a block copolymer, the remainder being copolymerized propylene. The sutures are characterized by an excellent balance of properties.

THE PRIOR ART

Usher, U.S. Pat. No. 3,105,493, discloses sutures made of high density polyethylene polymers which can contain small amounts of other olefins, such as propylene, copolymerized with the ethylene.

Northey, in U.S. Pat. No. 3,359,983, discloses sutures made of either polyethylene or polypropylene homopolymers.

Oppenlander, in U.S. Pat. No. 3,505,164, discloses conjugate fibers composed of polypropylene and ethylene-propylene copolymer.

Cash et al., in U.S. Pat. No. 3,432,514, discloses a compression molded disk made from a copolymer of 94 percent propylene and 6 percent ethylene (see Example II in Col. 5).

Listner, in U.S. Pat. No. 3,458,471, discloses stabilized filaments made from a variety of olefin polymers, including ethylene-propylene copolymers of unspecified proportions.

Ziegler et al., in U.S. Pat. No. 3,113,115, at Col. 1, lines 35 et seq., disclose various olefin copolymers, including ethylene-propylene copolymers. At Col. 11, lines 21-23, it is disclosed that the polymers disclosed in the patent can be spun into threads.

DETAILED DESCRIPTION OF THE INVENTION

The copolymer employed to produce the sutures of the invention is a random or block copolymer of ethylene and propylene containing only a small amount of polymerized ethylene, e.g., from about 0.3 to about 7, and preferably from about 0.5 to about 5, weight percent, the remainder being polymerized propylene, for random copolymers, and from about 2 to about 15, and preferably from about 4 to about 10, weight percent of polymerized ethylene, the remainder being polymerized propylene, for block copolymers. The molecular weight of the copolymer is such as to impart a melt flow of from about 0.5 to about 7 as determined by ASTM D-1238, Condition L. Ordinarily, a melt flow within this range will be obtained with weight average molecular weights of the order of about 200,000 to about 500,000. In many cases where it is desired to obtain the highest tensile strengths, the melt flow of the copolymer will be less than about 3.

The copolymer can contain the usual stabilizers against heat, ultraviolet, and oxidative degradation. Such stabilizers include hindered phenols, tertiary amines, and the like. The copolymer can also contain dyes, colorants, and lubricants.

The sutures of the invention are produced by extruding monofilaments of the copolymer by known procedures, drawing the extruded monofilaments to orient the polymer, and then subjecting the drawn monofilaments to an annealing/relaxing step. The basic procedure that can be employed is described by the Listner patent cited above (No. 3,630,205). Typical conditions that can be used to produce the sutures of the invention are shown below in the examples, wherein Listner's procedure is modified so as to use a three-stage draw.

The sutures of the invention can be produced in the usual sizes, e.g., from Size 2 down to Size 11/0. They can be attached to needles by the usual procedures, and can then be sterilized (as by using ethylene oxide) and packaged in sterile packs ready for use.

The following Examples illustrate the invention:

EXAMPLE 1

A random copolymer (A) containing about 1.3 weight percent polymerized ethylene and about 98.7 weight percent polymerized propylene was employed. The copolymer had the following properties:

| Melt Flow[1] | 2.0 |
|---|---|
| Molecular Weight[2] | $3 \times 10^5$ |

[1]By ASTM D-1238, Condition L
[2]Weight average molecular weight

The copolymer was extruded, drawn, and annealed under the conditions set forth below:

| A. Extrusion: (screw extruder: 1″ diam. 12/1 L/D0) | |
|---|---|
| block/die temp: | 409/431° F. |
| die diam/# holes: | 0.050″/1 |
| barrel pressure: | 1500 psi |
| pump pressure: | 1050 psi |
| throughput: | 376 gph (grams per hour) |
| quench water temp: | 75° F. |
| B. Drawing: (single-end godet rolls) | |
| 1st godet-speed/temp: | 27 fpm/170° F. |
| 2nd godet-speed/temp: | 160 fpm/210° F. |
| 3rd godet-speed/temp: | 180 fpm/77° F. |
| heated oven temp: | 300° F. |
| 4th godet-speed/temp: | 200 fpm/77° F. |
| (The drawing was done in three stages, with the heated oven being located between the 3rd and 4th godets.) | |
| C. Annealing: (forced air heated oven) | |
| 16% relax at 250° F. for 5 min | |
| heat set at 285° F. for 30 min | |

The extruded copolymer was drawn a total of 7.4X (before relaxation). The final product was a size 0 monofilament (diameter about 13.8 mils). After aging for one month, the tensile properties of the monofilament were the following:

| Tensile strength | 62,600 psi |
|---|---|
| Knot strength | 42,200 psi |
| Young's Modulus | 232,000 psi |

Typical tensile properties for commercial polypropylene size 0 monofilament suture material are the following:

| Tensile strength | 64,500 psi |
|---|---|
| Knot Strength | 41,300 psi |
| Young's Modulus | 473,000 psi |

EXAMPLES 2-8

Monofilament suture material was made from Polymer A (the ethylene-propylene random copolymer described in Example 1), Polymer B, ethylene-propylene random copolymer (about 97.8 weight percent propylene, about 2.2 weight percent ethylene-Melt Flow=5), Polymer C (random copolymer-about 95.8 weight percent propylene, about 4.2 weight percent ethylene-Melt Flow=1.0), Polymer D (random copolymer-about 95.8 weight percent propylene, about 4.2 weight percent ethylene-Melt Flow=3), and Polymer E (random copolymer-about 94.5 weight percent propylene, about 5.5 weight percent ethylene-Melt Flow=3.8). The extrusion, drawing, and annealing conditions are displayed in Table I. The fiber was cut into suture lengths, packaged, and ethylene oxide sterilized. Representative physical properties of the sterilized monofilaments are displayed in Table II. In Table II, the numbers in parentheses are values of typical commercial polypropylene sutures of comparable size. The overall draw ratio ($D_T$) is determined by the equation:

$$D_T = D_{ext}(1 - S/100)$$

wherein:

$$D_{ext} = \frac{\text{speed of IV Godet}}{\text{speed of I Godet}}$$

% S = % Shrinkage during annealing

TABLE I

| | EXTRUSION | | | | DRAWING | | | | | ANNEALING | | |
|---|---|---|---|---|---|---|---|---|---|---|---|---|
| | | | | | | | III | | IV | | | |
| | Block/ Die Temp. (°F.) | Die Dia./ # Holes (in./__) | Barrel/ Pump Dr. (psi) | Quench Water Temp (°F.) | I Godet Speed/ Temp (fpm/°F.) | II Godet Speed/ Temp (fpm/°F.) | Godet Speed/ Temp (fpm/°F.) | Heated Oven (in./°F.) | Godet Speed/ Temp (fpm/°F.) | % Relaxation | Anneal. Temp. (°F.) | Anneal. Time (min.) |
| Example 2 (Size 0) Polymer A | 399/412 | 0.04/1 | 1450/850 | 77 | 10/170 | 68/210 | 73/77 | 72/300 | 82/77 | 25 | 285 | 20 |
| Example 3 (Size 5/0) Polymer A | 398/412 | 0.03/1 | 1900/750 | 72 | 10/200 | 68/220 | 74/77 | 72/300 | 83/77 | 25 | 300 | 30 |
| Example 4 (Size 4/0) Polymer A | 398/431 | 0.03/1 | 1700/1400 | 75 | 27/170 | 180/210 | 205/77 | 72/300 | 260/77 | 25 | 300 | 30 |
| Example 5 (Size 0) Polymer B | 410/431 | 0.05/1 | 1600/600 | 78 | 27/170 | 160/210 | 180/77 | 72/300 | 200/77 | 25 | 300 | 30 |
| Example 6 (Size 0) Polymer C | 409/412 | 0.05/1 | 1300/400 | 78 | 10/100 | 52/110 | 65/130 | 72/250 | 75/77 | 16 | 265 | 10 |
| Example 7 (Size 2/0) Polymer D | 408/420 | 0.05/1 | 1700/350 | 63 | 10/120 | 45/140 | 54/77 | 72/250 | 65/77 | 16 | 265 | 20 |
| Example 8 (Size 0) Polymer E | 407/410 | 0.05/1 | 1600/200 | 78 | 10/100 | 59/110 | 63/130 | 72/250 | 75/77 | 16 | 265 | 10 |

TABLE II

| PROPERTY | EXAMPLE 2 Size 0 | EXAMPLE 3 Size 5/0 | EXAMPLE 4 Size 4/0 | EXAMPLE 5 Size 0 | EXAMPLE 6 | EXAMPLE 7 | EXAMPLE 8 |
|---|---|---|---|---|---|---|---|
| Diameter, mils | 15.34 (13.30) | 5.06 (5.30) | 7.68 (7.60) | 15.3 | 15.1 | 12.6 | 14.2 |
| Knot pull, lb. | 8.93 (7.60) | 1.13 (1.20) | 2.22 (2.40) | 6.3 | 6.2 | 3.9 | 6.0 |
| Knot-Intrinsic, psi | 42900 (41300) | 56140 (54400) | 47900 (52900) | 35,000 | 34,500 | 32,000 | 37,900 |
| Straight Pull, lb. | 12.28 (11.70) | 1.36 (2.00) | 3.07 (3.50) | 8.9 | 8.4 | 5.7 | 7.2 |
| Straight Intrinsic, psi | 66400 (64500) | 67730 (90700) | 66200 (77200) | 48,300 | 47,000 | 47,000 | 45,600 |
| Elongation, % | 91.50 (49.90) | 65.10 (47.60) | 58.45 (46.40) | 109 | 59 | 79 | 39 |
| Young's Modulus, psi | 260000 (473000) | 260000 (527000) | 259600 (533800) | 164,000 | 125,000 | 148,000 | 188,500 |
| Fatigue life (cycles) | 2141 (392) | 1019 (40) | 934 (203) | — | | | |
| Knot security (dry) | 3 throws (1/20 slip) (3) | 3 throws (3) | 3 throws (3) | — | | | |
| Memory | 0.88" (1.5") | 1.67" (0.94") | 1.39" (0.38") | — | | | |

The tensile properties (i.e., straight pull, Young's Modulus, and intrinsic) displayed on Table II were determined using an INSTRON tensile tester using the procedure of ASTM D-2256-66T. The knot strength was determined by the test method described in the U.S. Pharmocopeia, Vol. XVII, page 921. The settings on the Instron Tensile Tester used to determine the straight tensile, knot tensile, break elongation, and Young's modules were the following:

|  | Gauge Length | Chart Speed | Crosshead Speed |
|---|---|---|---|
| Tensile Strength | 1" | 5"/min | 1"/min |
| Knot Strength | 2" | 5"/min | 2"/min |
| Break Elongation | 1" | 5"/min | 1"/min |
| Young's Modulus | 5" | 20"/min | 5"/min |

The Fatigue Tests were carried out by the procedure of ASTM-D2176-63T. In the memory test, the sutures are carefully removed from their packages and the average distance between package "kinks" is measured. The knot security tst is carried out by the following procedure:

A loop of suture material is formed around a three-inch mandrel and a knot with varying number of squared throws tied by hand. The loop is cut on the opposite side of the mandrel from the knot, and the cut ends are clamped in the jaws of an Instron Tensile Tester. The knot is pulled apart with a crosshead speed of 2 inches/minute and will either slip or break. The lowest force at which slipping occurs is measured or, if no slipping occurs, the force required for breaking. Twenty knots are pulled apart for the force required for each size suture and for each number of throws.

A typical determination is made by tying 20 knots with two squared throws and pulling them apart. Assuming they all slip, 20 knots with three squared throws are tied and pulled apart. This process is continued with increasing throws until all 20 knots break cleanly without slipping. The forces are then computed separately for each throw to determine the average force and standard deviation at which absolute knot security can be obtained.

As the data in Table II illustrate, the ethylene-propylene copolymer sutures of the invention can retain to a substantial degree the desirable strength properties of comparably sized polypropylene sutures, while having a lower Young's Modulus (which is an indication, although not a direct measurement, of compliance). The sutures of this invention are perceived by most surgeons to be more compliant than are the comparably sized polypropylene sutures. This subjective feeling by surgeons, which is difficult to measure with precision by physical testing, is an important improvement over polypropylene homopolymer sutures. This improvement in performance is provided by a small proportion of copolymerized ethylene in the propylene polymer. It is surprising that the small amount of ethylene used, an amount too small to have a major effect on most measurable physical properties, has such a significant effect on the subjective feeling of compliance of the sutures made from the copolymers.

When comparing the sutures of this invention with polypropylene (homopolymer) sutures, the most appropriate comparisons are made between sutures of approximately the same size that are made from polymers having about the same molecular weights.

The sutures of this invention will ordinarily have properties within the ranges set forth in Table III:

TABLE III

| Tensile strength, psi | 40,000 to 110,000 |
|---|---|
| Knot strength, psi | 30,000 to 90,000 |
| Break elongation, % | 25 to 110 |
| Young's Modulus, psi | 100,000 to 400,000 |

A comparison of the fatigue life of the ethylene-propylene copolymer sutures with that of polypropylene sutures shows the former to possess a significantly longer life (as indicated by the number of cycles to failure). Consequently, the ethylene-propylene copolymer sutures may be considered preferable in surgical applications in which cyclic loading of the suture is expected.

EXAMPLES 9-10

Monofilament suture material was made from Polymer G (a block copolymer-about 7.5 weight percent ethylene and 92.5 weight percent propylene-Melt Flow 0.5), and Polymer H (random copolymer, about 1.6 weight percent ethylene and 98.4 weight percent propylene-Melt Flow 1.6). The extrusion conditions are shown in Table IV, and the annealing conditions and properties of the annealed fibers are shown in Table V. The fibers were allowed to relax 16% during the annealing.

TABLE IV

| | | PROCESSING CONDITIONS | | | |
|---|---|---|---|---|---|
| Example | Polymer | Extrusion Temp., °C. (Block/Die) | Draw Ratio | Take-up Speed ft./min. | Oven Temp. °F. |
| 9 | Polymer G | 220/223 | 8.6 | 86 | 200 |
| 10 | Polymer H | 210/216 | 8.4 | 84 | 300 |

TABLE V
ANNEALING CONDITIONS AND PROPERTIES OF ANNEALED FIBERS

| Example | Polymer | Annealing Temp., °F. | Annealing Time, Mins. | Diameter | Knot Strength, lb. | Tensile Strength, lb. | Elongation % | Young's Modulus, psi |
|---|---|---|---|---|---|---|---|---|
| 9 | Polymer G | 285 | 20 | 12.7 | 6.1 | 8.5 | 79 | 365,000 |
| 10 | Polymer H | 285 | 20 | 12.4 | 6.2 | 7.3 | 44 | 355,000 |

What is claimed:

1. A sterile surgical monofilament suture comprising an ethylene-propylene copolymer, said copolymer containing a small amount of copolymerized ethylene, the balance being copolymerized propylene, said copolymerized ethylene being present in an amount sufficient to impart a significant reduction in Young's Modulus to the suture compared with a comparable propylene homopolymer suture, wherein said copolymer is a block copolymer containing from about 2 to about 15 weight percent polymerized ethylene.

2. The sterile suture of claim 1 wherein said copolymer has a melt flow determined by ASTM D-1238, condition L, of from about 0.5 to about 7.

3. The sterile suture of claim 2 wherein the copolymer has a melt flow of less than about 3.

4. The sterile suture of claim 2 wherein said suture has the following properties:

TABLE III

| Tensile strength, psi | 40,000 to 110,000 |
|---|---|
| Knot strength, psi | 30,000 to 90,000 |
| Break elongation, % | 25 to 110 |
| Young's Modulus, psi | 100,000 to 400,000 |

5. The sterile suture of claim 3 wherein said suture has the following properties:

TABLE III

| Tensile strength, psi | 40,000 to 110,000 |
|---|---|
| Knot strength, psi | 30,000 to 90,000 |
| Break elongation, % | 25 to 110 |
| Young's Modulus, psi | 100,000 to 400,000 |

6. A sterile needled suture comprising the suture of claim 1 attached to a needle.

* * * * *